United States Patent
Tao et al.

(10) Patent No.: US 12,056,796 B2
(45) Date of Patent: Aug. 6, 2024

(54) SYSTEM AND METHOD FOR HIGH FIDELITY COMPUTED TOMOGRAPHY

(71) Applicant: Mayo Foundation for Medical Education and Research, Rochester, MN (US)

(72) Inventors: Shengzhen Tao, Rochester, MN (US); Shuai Leng, Rochester, MN (US); Cynthia H. McCollough, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 719 days.

(21) Appl. No.: 17/256,404

(22) PCT Filed: Jun. 28, 2019

(86) PCT No.: PCT/US2019/039725
§ 371 (c)(1),
(2) Date: Dec. 28, 2020

(87) PCT Pub. No.: WO2020/006352
PCT Pub. Date: Jan. 2, 2020

(65) Prior Publication Data
US 2021/0319600 A1    Oct. 14, 2021

Related U.S. Application Data

(60) Provisional application No. 62/692,350, filed on Jun. 29, 2018.

(51) Int. Cl.
| | |
|---|---|
| *G06T 11/00* | (2006.01) |
| *A61B 6/00* | (2006.01) |
| *A61B 6/03* | (2006.01) |
| *G06T 5/50* | (2006.01) |
| *G06T 5/70* | (2024.01) |

(52) U.S. Cl.
CPC .......... *G06T 11/008* (2013.01); *A61B 6/032* (2013.01); *A61B 6/5211* (2013.01); *A61B 6/5258* (2013.01); *G06T 5/50* (2013.01); *G06T 5/70* (2024.01); *G06T 11/005* (2013.01); *G06T 2207/10081* (2013.01); *G06T 2211/408* (2013.01); *G06T 2211/424* (2013.01)

(58) Field of Classification Search
CPC ..... G06T 5/002; G06T 11/003; G06T 11/005; G06T 11/008; G06T 2211/408; G06T 2211/424; G06T 5/70; A61B 6/5258
See application file for complete search history.

(56) References Cited

U.S. PATENT DOCUMENTS

| | | | |
|---|---|---|---|
| 2016/0055658 A1* | 2/2016 | Liang et al. | G06T 11/006 382/131 |
| 2017/0221234 A1 | 8/2017 | Chen | |
| 2018/0101948 A1 | 4/2018 | Yu et al. | |
| 2018/0114314 A1 | 4/2018 | Butler et al. | |

FOREIGN PATENT DOCUMENTS

WO    2017193122 A1    11/2017

OTHER PUBLICATIONS

Alvarez R E et al. 1976 Energy-selective reconstructions in x-ray computerized tomography Phys Med Biol 21 733-44.
Atak H et al. 2015 Dual energy CT with photon counting and dual source systems: comparative evaluation Phys Med Biol 60 8949-75.
Boyd S, et al. 2010 Distributed Optimization and statistical learning via the alternating direction method of multipliers Found Trends Mach Learn 3 1-122.
Carmi R, et al. 2005 Material separation with dual-layer CT IEEE Nuclear Science Symposium vol. 4 pp. 1876-1878.
Chen G H, et al. 2008 Prior image constrained compressed sensing (PICCS): A method to accurately reconstruct dynamic CT images from highly undersampled projection data sets Med Phys 35 660-3.
Chen G H, et al. 2009 Temporal resolution improvement using PICCS in MDCT cardiac imaging Med Phys 36 2130-5.
Choi J, et al. 2013 A unified statistical framework for material decomposition using multienergy photon counting x-ray detectors Med Phys 40 091913.
Clark D P et al. 2014 Spectral diffusion: an algorithm for robust material decomposition of spectral CT data Phys Med Biol 59 6445-66.
Coursey C A, et al. 2010 Dual-energy multidetector CT: how does it work, what can it tell US, and when can we use it in abdominopelvic imaging? Radiographics 30 1037-55.
Dong X, et al. 2014 Combined iterative reconstruction and image-domain decomposition for dual energy CT using total-variation regularization Med Phys 41 051909.
Ferda J, et al. 2009 The assessment of intracranial bleeding with virtual unenhanced imaging by means of dual-energy CT angiography Eur Radiol 19 2518-22.

(Continued)

*Primary Examiner* — Andrew W Johns
(74) *Attorney, Agent, or Firm* — Quarles & Brady LLP

(57) ABSTRACT

A system and method is provided for high fidelity multi-energy CT processing. This system and method exploits prior knowledge, where prior knowledge may include redundant information existing in the CT images, such as spatial redundancy between a thick slice and a thin slice encompassed by or close to the thick slice, or the spatio-spectral redundancy between the image output of multi-energy CT processing and the source multi-energy CT images. The system and method retains structural details, spatial resolution, spectral fidelity, and noise texture while achieving noise reduction. The method reduces image noise and increases the contrast-to-noise ratio in processed images, while simultaneously maintaining image details and natural appearance of the image to enhance detectability and facilitate reader acceptance.

18 Claims, 10 Drawing Sheets

(56) References Cited

OTHER PUBLICATIONS

Flohr T G, et al. 2006 First performance evaluation of a dual-source CT (DSCT) system Eur Radiol 16 256-68.

Foygel Barber, R, et al. 2016 An algorithm for constrained one-step inversion of spectral CT data Phys Med Biol 61 3784-818.

Glazebrook K N, et al. 2011 Identification of intraarticular and periarticular uric acid crystals with dual-energy CT: initial evaluation Radiology 261 516-24.

Harms J, et al. 2016 Noise suppression for dual-energy CT via penalized weighted least-square optimization with similarity-based regularization Med Phys 43 2676.

Heismann B J, et al. 2003 Density and atomic number measurements with spectral x-ray attenuation method J Appl Phys 94 2073-9.

Hounsfield G. N. 1973 Computerized transverse axial scanning (tomography). I. Description of system Br J Radiol 46 1016-22.

International Searching Authority. International Search Report and Written Opinion for application PCT/ US2019/039725. Mailed on Sep. 30, 2019. 13 pages.

Johnson T R C, et al. 2007 Material differentiation by dual energy CT: initial experience Eur Radiol 17 1510-7.

Kalender W A, et al. 1986 Evaluation of a Prototype Dual-Energy Computed Tomographic Apparatus . 1. Phantom Studies Med Phys 13 334-9.

Kalender W A, et al. 1988 An algorithm for noise suppression in dual energy CT material density images IEEE Trans Med Imaging 7 218-24.

Korn A, et al. 2011 Dual energy CTA of the carotid bifurcation: Advantage of plaque subtraction for assessment of grade of the stenosis and morphology Eur J Radiol 80 E120-E5.

Lauzier P T, et al. 2012 Prior image constrained compressed sensing: Implementation and performance evaluation Med Phys 39 66-80.

Le HQ et al. 2011 Least squares parameter estimation methods for material decomposition with energy discriminating detectors Med Phys 38 245-55.

Leng S, et al. 2008 High temporal resolution and streak-free four-dimensional cone-beam computed tomography Phys Med Biol 53 5653-73.

Leng S, et al. 2011 Noise reduction in spectral CT: Reducing dose and breaking the trade-off between image noise and energy bin selection Med Phys 38 4946-57.

Leng S, et al. 2015 Maximizing iodine contrast-to-noise ratios in abdominal CT imaging through use of energy domain noise reduction and virtual monoenergetic dual-energy CT Radiology 276 562-70.

Leng S, et al. 2017 Ultra-high spatial resolution, multi-energy CT using photon counting detector technology Proc SPIE Int Soc Opt Eng 10132.

Liu J, et al. 2016 TICMR: Total image constrained material reconstruction via nonlocal total variation regularization for spectral CT IEEE Trans Med Imaging 35 2578-86.

Liu X, et al. 2009 Quantitative imaging of element composition and mass fraction using dual-energy CT: Three-material decomposition Med Phys 36 1602-9.

Liu, Y. et al. A joint iterative reconstruction algorithm for dual energy CT using ADMM. The 13th International Meeting on Fully Three-Dimensional Image Reconstruction in Radiology and Nuclear Medicine; Rhode Island. 2015. p. 511-514.

McCollough C H, et al. 2015 Dual- and multi-energy CT: Principles, technical approaches, and clinical applications Radiology 276 637-53.

Mendonca P R, et al. 2014 A flexible method for multi-material decomposition of dual-energy CT images IEEE Trans Med Imaging 33 99-116.

Morhard D, et al. 2009 Cervical and cranial computed tomographic angiography with automated bone removal dual energy computed tomography versus standard computed tomography Invest Radiol 44 293-7.

Niu T, et al. 2014 Iterative image-domain decomposition for dual-energy CT Med Phys 41 041901.

Primak A N, et al. 2007 Noninvasive differentiation of uric acid versus non-uric acid kidney stones using dual-energy CT Acad Radiol 14 1441-7.

Qi Z, et al. 2010 Dramatic noise reduction and potential radiation dose reduction in breast cone-beam CT imaging ssing prior image constrained compressed sensing (PICCS) Med Phys 37, No. 6 Part 7, 3443.

Qu M, et al. 2012 Toward biphasic computed tomography (CT) enteric contrast: material classification of luminal bismuth and mural iodine in a small-bowel phantom using dual-energy CT J Comput Assist Tomogr 36 554-9.

Rajendran, K., et al. "Quantitative imaging of excised osteoarthritic cartilage using spectral CT." European radiology 27.1 (2017): 384-392.

Ramírez-Giraldo J, et al. Non-convex prior image constrained compressed sensing (NCPICCS). In: Samei E, Pelc NJ, eds. Proceedings of SPIE: medical imaging 2010—physics of medical imaging. vol 7622. Bellingham, Wash: International Society for Optics and Photonics, 2010; 76222C.

Sawatzky A, et al. 2014 Proximal ADMM for multi-channel image reconstruction in spectral X-ray CT IEEE Trans Med Imaging 33 1657-68.

Schirra C O, et al. 2013 Statistical reconstruction of material decomposed data in spectral CT IEEE Trans Med Imaging 32 1249-57.

Schmidt T G, et al. 2017 A spectral CT method to directly estimate basis material maps from experimental photon—counting data IEEE Trans Med Imaging 36 1808-19.

Shikhaliev P M 2008 Energy-resolved computed tomography: first experimental results Phys Med Biol 53 5595-613.

Silva A C, et al. 2011 Dual-energy (spectral) CT: applications in abdominal imaging Radiographics 31 1031-46.

Stierstorfer K, et al. 2004 Weighted FBP—a simple approximate 3D FBP algorithm for multislice spiral CT with good dose usage for arbitrary pitch Phys Med Biol 49 2209-18.

Symons R, et al. 2017 Photon-counting CT for simultaneous imaging of multiple contrast agents in the abdomen: An in vivo study Med Phys 44 5120-7.

Tao S, et al. 2016 Partial Fourier and parallel MR image reconstruction with integrated gradient nonlinearity correction Magn Reson Med 75 2534-44.

Wang M, et al. 2016 An adaptive reconstruction algorithm for spectral CT regularized by a reference image Phys Med Biol 61 8699-719.

Wang Q, et al. 2017 Locally linear constraint based optimization model for material decomposition Phys Med Biol 62 8314-40.

Xi Y, et al. 2015 United iterative reconstruction for spectral computed tomography IEEE Trans Med Imaging 34 769-78.

Xue Y, et al. 2017 Statistical image-domain multimaterial decomposition for dual-energy CT Med Phys 44 886-901.

Yu Z C, et al. 2016 Evaluation of conventional imaging performance in a research whole-body CT system with a photon-counting detector array Phys Med Biol 61 1572-95.

Yu Z C, et al. 2016 Spectral prior image constrained compressed sensing (spectral PICCS) for photon-counting computed tomography Phys Med Biol 61 6707-32.

Yu Z, et al. 2016 How low can we go in radiation dose for the data-completion scan on a research whole-body photon-counting computed tomography system J Comput Assist Tomogr 40 663-70.

Zhang H, et al. 2017 Iterative reconstruction for dual energy CT with an average image-induced nonlocal means regularization Phys Med Biol 62 5556-74.

Zhang Y, et al. 2016 Spectral CT reconstruction with image sparsity and spectral mean IEEE Trans Comput Imaging 2 510-23.

Zhao W, et al. 2016 Using edge-preserving algorithm with non-local mean for significantly improved image-domain material decomposition in dual-energy CT Phys Med Biol 61 1332-51.

Zhou W, et al. 2017 Lung nodule vol. quantification and shape differentiation with an ultra-high resolution technique on a photon-

(56) References Cited

OTHER PUBLICATIONS counting detector computed tomography system J Med Imaging (Bellingham) 4 043502.

* cited by examiner

SYSTEM AND METHOD FOR HIGH FIDELITY COMPUTED TOMOGRAPHY

CROSS-REFERENCES TO RELATED APPLICATIONS

This application represents the national stage entry of PCT/US2019/039725 filed on Jun. 28, 2019 and claims the benefit of U.S. Provisional Patent Application Ser. No. 62/692,350 filed on Jun. 29, 2018 the contents of which is herein incorporated by reference in its entirety.

STATEMENT REGARDING FEDERALLY SPONSORED RESEARCH

This invention was made with government support under EB016966 awarded by the National Institutes of Health. The government has certain rights in the invention.

BACKGROUND

X-ray computed tomography (CT) is widely utilized in clinics and is the first-choice imaging modality for many clinical tasks. The diagnostic quality of a CT image is highly dependent on image noise and contrast-to-noise (CNR) ratio. For many CT applications, there is an intrinsic trade-off between slice thickness and image noise. Conventional x-ray (CT) also typically acquires mean x-ray attenuation measurements using a single energy spectrum. However, materials of different atomic compositions and mass densities can appear similar in a single-energy CT image due to the potential for the materials to end up with the same CT number, which makes it difficult to differentiate them using conventional CT. Dual-energy or multi-energy CT, also known as spectral CT, complements conventional CT by obtaining x-ray attenuation measurements at two or more energy spectra. Multi-energy CT allows for identification and quantification of different materials by exploiting the dependence of the x-ray attenuation of each material on x-ray energy.

Dual-energy CT (a subtype of multi-energy CT with two energies), has enabled a wide range of clinical applications to benefit patient diagnosis and care. Multi-energy CT (e.g. three or more energies), similarly allows for new diagnostic methods and clinical applications. One example to achieve multi-energy CT is to use the photon counting detectors, which are capable at the present time of producing 4-8 different energy bins.

Multi-energy CT-based quantitative imaging exploits differences in x-ray attenuation among different materials. In CT images, because different materials cause different levels of x-ray scattering and absorption, proper calibration of image pixel values versus x-ray beam energy can be used to qualitatively and quantitatively evaluate an imaged object's material composition. The process of differentiating various materials (either quantitatively or qualitatively) based on its x-ray attenuation property using multi-energy CT data, as well as the process of using the material information to enhance certain image feature, is called multi-energy processing. Multi-energy processing can be performed using dual-energy or multi-energy CT. In general, multi-energy processing can include both the process of material decomposition, and the process of synthesizing other types of images to enhance certain image features using the results of material decomposition.

When performing multi-energy processing, a major limitation of multi-energy CT is the high image noise and compromised CNR. First, the applied radiation dose must be divided into multiple energy bins in multi-energy CT, which increases image noise within each energy-specific image. In addition, the mathematical process used to identify and quantify different materials, i.e., material decomposition is known to increase image noise.

Due to its ill-conditioned nature, the multi-energy CT process of material decomposition is intrinsically susceptible to noise amplification and this process usually amplifies noise in the output images such as the material-specific images. Hence, material-specific images can be contaminated by the presence of strong noise, which compromises the conspicuity of small objects, and hinders the delineation of anatomical regions of interest and associated pathology. The noise amplification effect can also affect the images derived from the material specific images, such as the virtual monoenergetic/monochromatic images, especially at lower (e.g., 50 keV) or higher keV (e.g., 120 keV).

Slice thickness and image noise are also related. A thick slice image may be reconstructed using more photons and therefore usually has lower image noise. This principle applies at least to both conventional CT and multi-energy CT. To meet the clinical demand for low image noise in many applications, a large image slice thickness is typically utilized. However, a large image thickness can aggregate the partial volume effect, which causes the key anatomical structure and pathology of interest to be mixed together with background tissue, and therefore obscures the visibility of these key features, compromising their CNR. A thinner slice thickness can reduce the partial volume effect, but suffers from increased image noise, which also compromises the CNR of these key image features. These challenges limit the diagnostic value and usefulness of CT images for a wide range of clinical applications, including head, chest, abdomen, extremity, and interventional CT applications with or without contrast agent injections. These issues are present in both single energy CT and multi-energy CT.

Thus there remains a need for high fidelity CT imaging where reducing noise and reducing partial volume effects will still retain structural detail and/or high image resolution in the reduced noise image.

SUMMARY OF THE DISCLOSURE

The present disclosure addresses the aforementioned drawbacks by providing a system and method for high fidelity CT data processing. The system and method exploit redundant CT image information in order to reduce image noise while reducing partial volume effects, such as by generating a thin slice CT image with reduced partial volume effects without increased noise. For multi-energy CT data processing, the system and method exploits spatiospectral data redundancy within a multi-energy CT data set to retain structural details in the output of multi-energy CT processing while reducing image noise in them.

In one configuration of the present disclosure, a method is provided for reducing noise in an image obtained using a computed tomography (CT) system. The method includes accessing, with a computer system, CT data acquired from a subject using the CT system. The CT data include a first image of the subject and a second image of the subject, and the first image and the second image contain redundant data. The method also includes generating with the computer system a denoised image having reduced noise relative to the first image by: inputting the first image and the second image to an objective function that includes a regularization term having a first component and a second component; the first component of the regularization term is a total variation of the first image and the second component of the regularization term exploits the redundant data in the first image and the second image by promoting sparsity in a difference between the first image and the second image. The method also includes minimizing the objective function in order to iteratively denoise the first image, generating output as the denoised image.

In one configuration of the present disclosure, a system is provided for reducing noise in an image obtained using a computed tomography (CT) system. The system includes a computer system configured to access CT data acquired from a subject using the CT system. The CT data include a first image of the subject and a second image of the subject; where the first image and the second image contain redundant data. The computer system is also configured to generate a denoised image having reduced noise relative to the first image by: inputting the first image and the second image to an objective function that includes a regularization term having a first component and a second component; the first component of the regularization term comprises a total variation of the first image and the second component of the regularization term exploits the redundant data in the first image and the second image by promoting sparsity in a difference between the first image and the second image; and minimizing the objective function in order to iteratively denoise the first image, generating output as the denoised image.

In one configuration of the present disclosure, a method is provided for determining a material decomposition using a computed tomography (CT) system. The method includes imaging a subject with the CT system using at least two different energy levels to acquire CT data associated with each of the energy levels. Multi-energy CT images are then reconstructed from the acquired CT data associated with each of the energy levels. Multi-energy processing is then performed based upon the image data, by minimizing an objective function that includes spatiospectral similarity between an image output of multi-energy processing and the multi-energy CT image. Alternatively, if images derived from the multi-energy CT processing, such as the virtual monoenergetic images, are of interest, the generation of these derived images can be performed by minimizing an objective function that includes spatiospectral similarity between these derived images and the multi-energy CT images.

In another configuration of the present disclosure, a method is provided for processing the direct and indirect outputs from any arbitrary material decomposition method to reduce noise or increase contrast-to-noise ratio in them. In this case, the multi-energy CT data can first be processed using any arbitrary multi-energy CT processing techniques. Their direct or indirect outputs, such as material specific images or virtual monoenergetic images, can then be used as initial estimates, or serve as the inputs to the present method, which exploits the spatiospectral data redundancy between these images and the multi-energy CT images to reduce image noise and increase CNR, while retaining image details.

In one configuration of the present disclosure, a system is provided for performing multi-energy processing using a computed tomography (CT) system. The system includes a photon counting CT system configured to image a subject using at least two different energy levels to acquire CT data associated with each of the energy levels. A computer system is also provided and configured to reconstruct the acquired CT data associated with each of the energy levels to produce multi-energy CT image data associated with each of the energy levels. The computer system also performs multi-energy processing of the image data where an objective function is minimized that includes spatiospectral similarity between an image output of multi-energy processing and the multi-energy CT image. The computer also performs denoising of images directly or indirectly derived from multi-energy data sets by minimizing an objective function that includes spatiospectral similarity between the multi-energy CT images and the images derived from multi-energy data sets.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
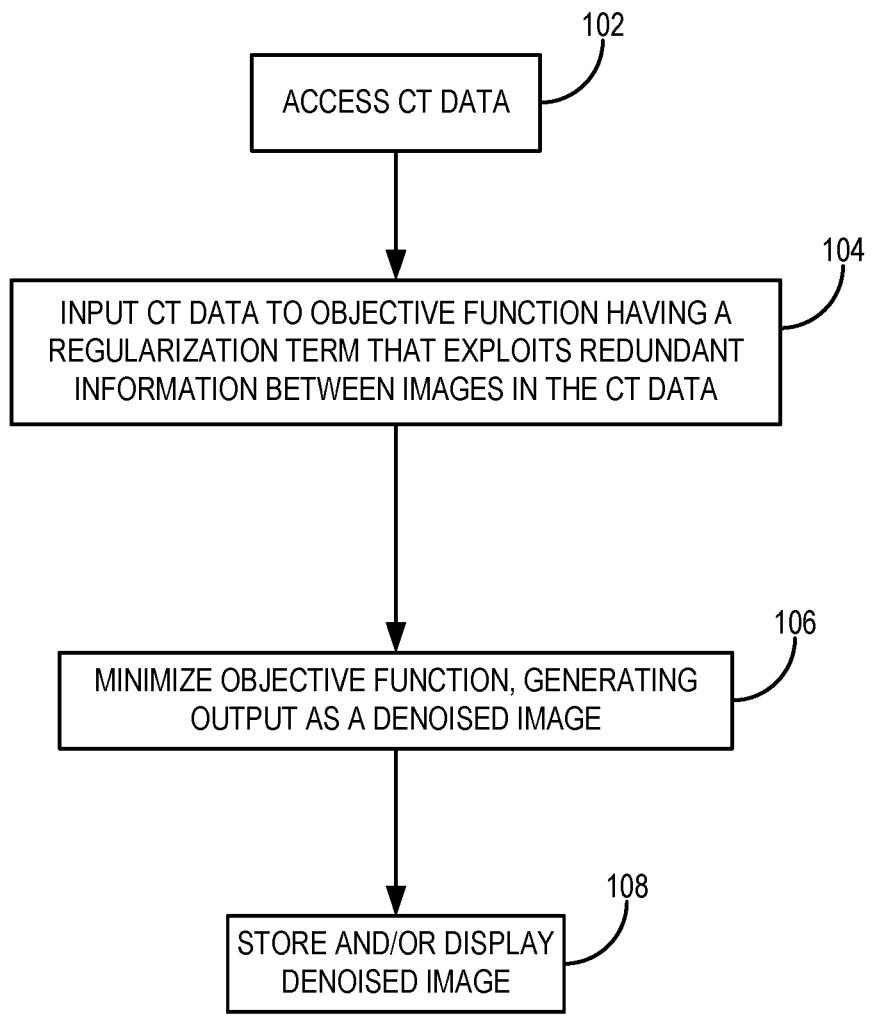
FIG. 1 is a flowchart setting forth the steps of an example method for denoising an image, or otherwise improving the image quality of an image, obtained with a CT system based on exploiting redundant information between the image and another image obtained with the CT system.

Described here are systems and methods for improving the quality of images obtained using a computed tomography (CT) system, which may be a single energy CT system or a multi-energy CT system. As an example, the quality of an image is improved by denoising the image, increasing the contrast-to-noise ratio (CNR) of the image, or both.

In general, the systems and methods described in the present disclosure exploit redundant data between a first image and a second image in order to denoised or otherwise improve the quality of the first image. As one example, the first image can be an image with a thinner slice thickness than the second image. In these examples, the redundant data can include spatial redundancy between the first and second image, such as structural similarity between the images. As another example, the first image can be a material-specific image (e.g., a material basis image) and the second image can be a multi-energy image. In these examples, the redundant data can include spatial redundancy, spectral redundancy, or spatiospectral redundancy between the first image and the second image.

In one configuration of the present disclosure, high fidelity CT imaging is achieved using prior knowledge. Prior knowledge may include exploiting redundant information existing in the CT images. In a non-limiting example, redundant information includes information along the slice increment direction. A first, thin slice thickness CT image may be generated with reduced partial volume effects and without increase image noise, therefore with improved CNR. Dose reduction may be achieved while maintaining the same image quality. A second, high resolution image may be generated with reduced image noise, which can be relevant for applications requiring high spatial fidelity, or the system and method may be used to reduce patient dose without sacrificing image quality and diagnostic outcome. Spatial image resolution may also be preserved in all directions, along with the natural appearance of CT images.

In another configuration of the present disclosure, an image-domain material decomposition algorithm that exploits spatiospectral data redundancy between the decomposition basis images (e.g., material specific images, electron density images, photoelectric effect images, virtual monoenergetic images) and the spectral CT images is provided. This algorithm includes reducing image noise and increasing the contrast-to-noise ratio in multi-energy CT, while simultaneously preserving image details, maintaining the natural appearance of the image to enhance detectability, and facilitating reader acceptance. The appearance of the image, or the noise texture of the image, can be evaluated using its noise power spectra, which represent the power or energy distribution of image noise as a function of spatial frequency.

A natural appearance refers to noise power spectra spanning across a desirable spatial frequency range, similar as those of standard CT images. A modified or unnatural noise texture usually features more loss of noise energy in the high frequency component, causing a shift of noise power spectra toward lower frequency range.

In some configurations, the image-domain material decomposition approach produces decomposition basis images from CT images measured with different energy spectra. Using material-specific images as an example of decomposition basis images, this algorithm exploits redundant information and structural similarities between the individual material-specific images and the measured spectral CT images to reduce the noise present in the material-specific images while preserving structural details and spatial resolution. Multiple normalization schemes may be used to enable comparison between material-specific images and multi-energy images and consequently reduce image noise in the material-specific images. A blending technique may be used to achieve natural image appearance and noise texture, consequently improving detectability and reader acceptance. In contrast to this approach, many conventional noise reduction techniques change the noise texture and consequently sacrifice detectability even at lower image noise.

The output of multi-energy CT processing may include the direct and indirect output of multi-energy CT data processing or related processes, such as material-specific images, virtual monoenergetic images, electron density images, effective atomic number images, Compton effect images, and photoelectric effect images. This data redundancy can be found between the direct output of material decomposition (e.g., individual material-specific images) and the source multi-energy CT images. This data redundancy can also be found between the images derived from multi-energy CT processing such as virtual monoenergetic images and the source multi-energy CT images.

The system and method of the present disclosure can be implemented to directly treat multi-energy CT data processing such as material decomposition, generation and processing of virtual monoenergetic images as an integrated process by solving a regularized optimization problem with spectral CT images measured with different energy spectra as inputs. The method reduces image noise and increases the contrast-to-noise ratio in multi-energy CT material decomposition or related analysis, while simultaneously maintaining the natural appearance of the output image to enhance detectability and facilitate reader acceptance. The system and method can also be used to denoise different types of multi-energy processing output images from any arbitrary multi-energy processing method. These output images can include, but are not limited to virtual monoenergetic (monochromatic) images, electron density images and effective atomic number images.

In another configuration of the present disclosure, a denoising and image processing framework that exploits spatiospectral data redundancy and structural similarity between the multi-energy CT images and the images derived from multi-energy CT data processing is provided that includes reducing image noise and increasing the contrast-to-noise ratio in the images derived from multi-energy CT data processing. This method can be applied to direct or indirect output of relevant multi-energy CT processing such as the material specific images, virtual monoenergetic images, electron density images and the effective atomic number images, while preserving image details, spatial resolution and noise texture of the original images.

In one configuration of the present disclosure, the multi-energy CT processing algorithm can be performed in projection space, image space, or both. The algorithm is applicable to all types of multi-energy CT, including but not limited to techniques using either energy-integrating detectors or photon-counting detectors. Input data to the proposed algorithm can in some instances include threshold data or bin data. Tunable parameters to balance noise reduction and noise texture may also be included.

High-Level Flowchart

Referring now to FIG. 1, a flowchart is illustrated as setting forth the steps of an example method for denoising an image, or otherwise improving the image quality of an image, obtained with a CT system based on exploiting redundant information between the image and another image obtained with the CT system.

The method includes accessing CT data with a computer system, as indicated at step 102. The CT data may be accessed by retrieving previously acquired CT data from a memory or other data storage device or medium. As another example, the CT data may be accessed by acquiring such data with a CT system and communicating or otherwise transmitting the acquired CT data to the computer system, which may be a part of the CT system. The CT data may include raw data acquired with the CT system, images reconstructed from raw data acquired with the CT system, qualitative or quantitative images generated from reconstructed images (e.g., output from a multi-energy processing), or combinations thereof. The CT data may include single energy CT data, multi-energy CT data, or both.

In general, the CT data includes first data and second data. The first data may include a first image of a subject and the second data may include a second image of the subject. As described above, the first image and the second image share redundant information, which may include spatial redundancy, spectral redundancy, or spatiospectral redundancy.

As one example, the first image may be a thin slice image and the second image may be a thick slice image that has a thicker slice thickness than the first image, but otherwise shares common spatial information with the first image. For instance, the first image may correspond to a thin slice that is spatially contained within the thicker slice associated with the second image.

As another example, the first image may be an image output from a multi-energy processing and the second image may be a multi-energy image. For instance, the first image may be a material-specific image, a virtual monoenergetic image, an electron density image, an effective atomic number image, a Compton effect image, a photoelectric effect image, or other such image generated from a multi-energy processing.

The redundant data between the first image and the second image can be exploited to reduce noise, or otherwise improve the image quality, of the first image. As indicated at step 104, the first image and the second image are input to an objective function. The objective function generally includes a data consistency term and a regularization term. The regularization term preferably includes a first component and a second component. The first component includes a total variation of the first image, and in some instances can include other norms or transformations of the first image. The second component promotes sparsity in a difference between the first image and the second image in order to exploit the redundant data in the first and second images. As one example, the second component can implement a total variation of the difference between the first and second images; however, other norms or transformations of the difference between the first and second images may also be used in some instances. The first and second components can be weighted to control a balance between the two components on the regularization term.

The objective function is then minimized using a computer system in order to iteratively reduce noise in the first image, or to otherwise improve the image quality of the first image, as indicated at step 106. That is, minimizing the objective function generates output as the denoised image, or otherwise improved image. This output image can then be stored for later use, or displayed to a user, as indicated at step 108.

Multi-Energy CT Example(s)

Figure 2:
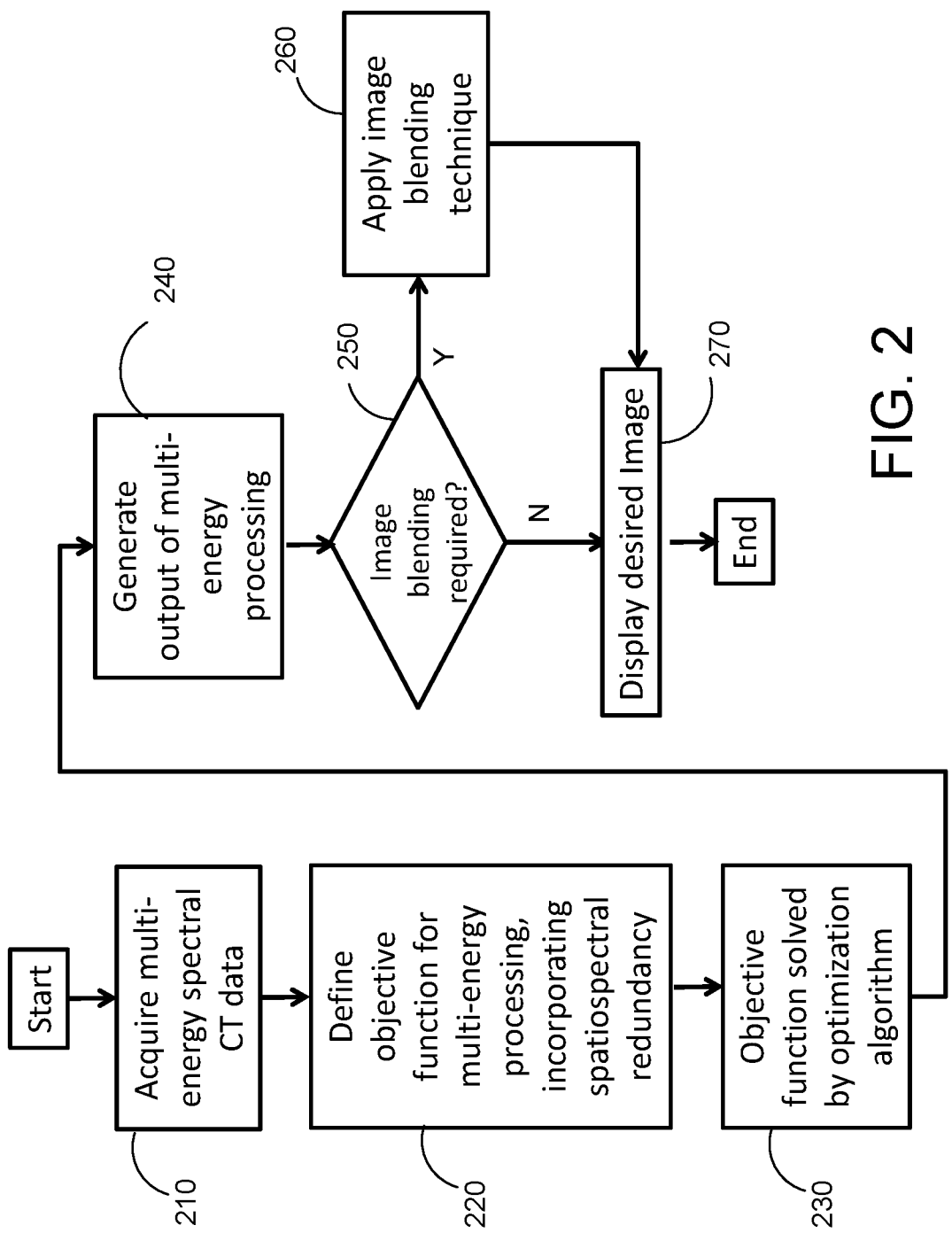
FIG. 2 is a flowchart depicting one configuration of the present disclosure, in which multi-energy processing is performed using multi-energy CT data by solving an optimization problem with its objective function incorporating the spatiospectral data redundancy between the multi-energy CT images and the decomposition basis images.

Referring particularly now to FIG. 2, a flowchart depicting one configuration of the present disclosure is provided. Multi-energy CT image data are acquired at step 210. Multi-energy CT data processing begins at step 220 by designing an objective function for multi-energy processing which incorporates the spatiospectral redundancy between the decomposition basis images (or images related to decomposition basis images) and the measured multi-energy CT images, and proceeds by the solution to this objective function being performed by an optimization algorithm at 230. The output of multi-energy processing is updated at 240 based upon the results of the iterative optimization from step 230. A user may select to perform image blending at step 250. Since noise reduction algorithms, especially total variation-based algorithms, can change image texture and create patchy looking images, a linear blending technique to combine the output of the present method with a standard least-squares based decomposition may be used at 260 to maintain the original image texture while reducing noise. A final image or data output reflecting the material composition of the subject being imaged is displayed at 270.

Figure 3:
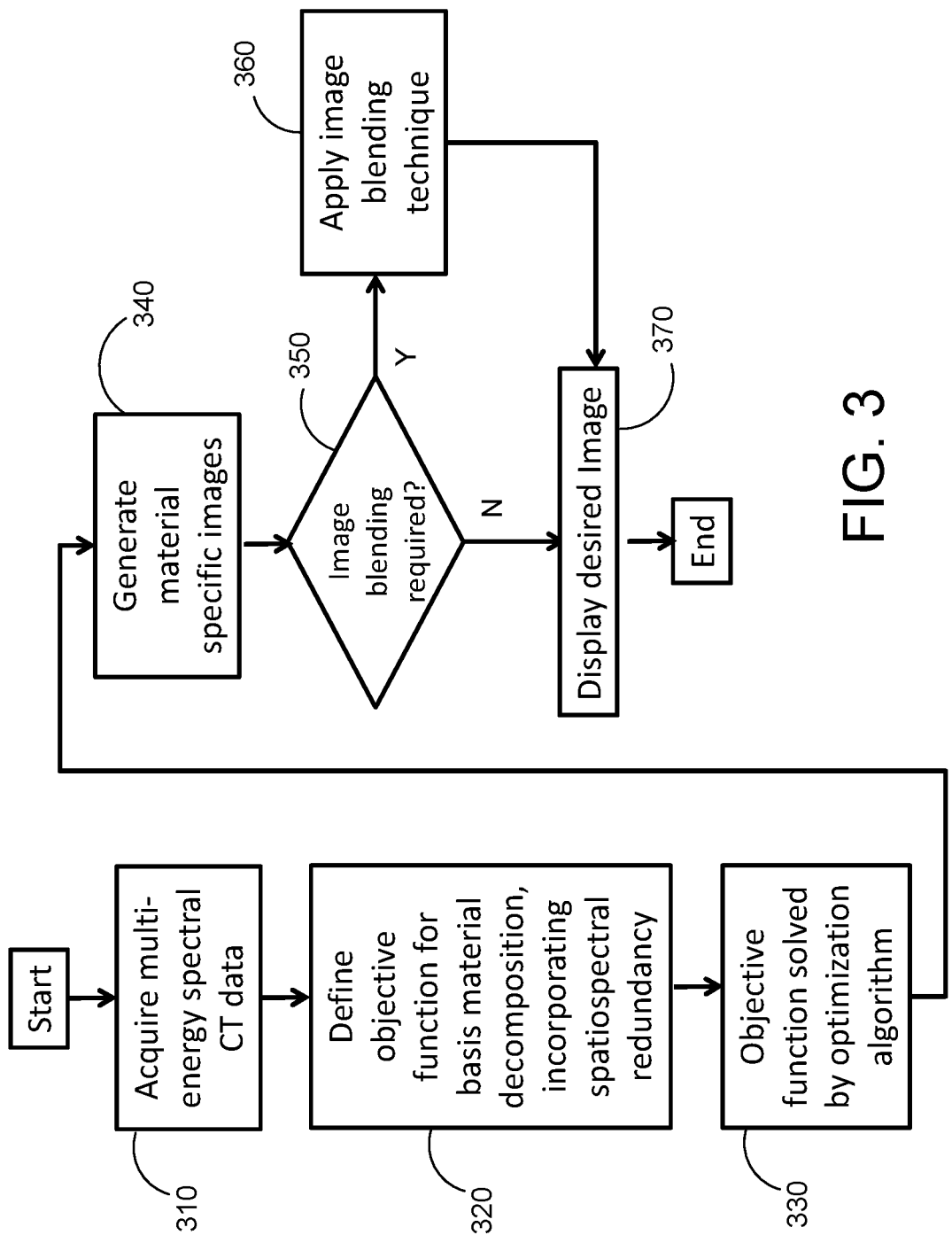
FIG. 3 is a flowchart depicting one example of the framework shown in FIG. 2, where the multi-energy processing refers to basis material based decomposition.

Referring now to FIG. 3, a flowchart depicting one example of the framework shown in FIG. 2 is provided. In this case, the multi-energy processing refers to basis material decomposition, and the output refers to material-specific images such as iodine, soft tissue images.

Figure 4:
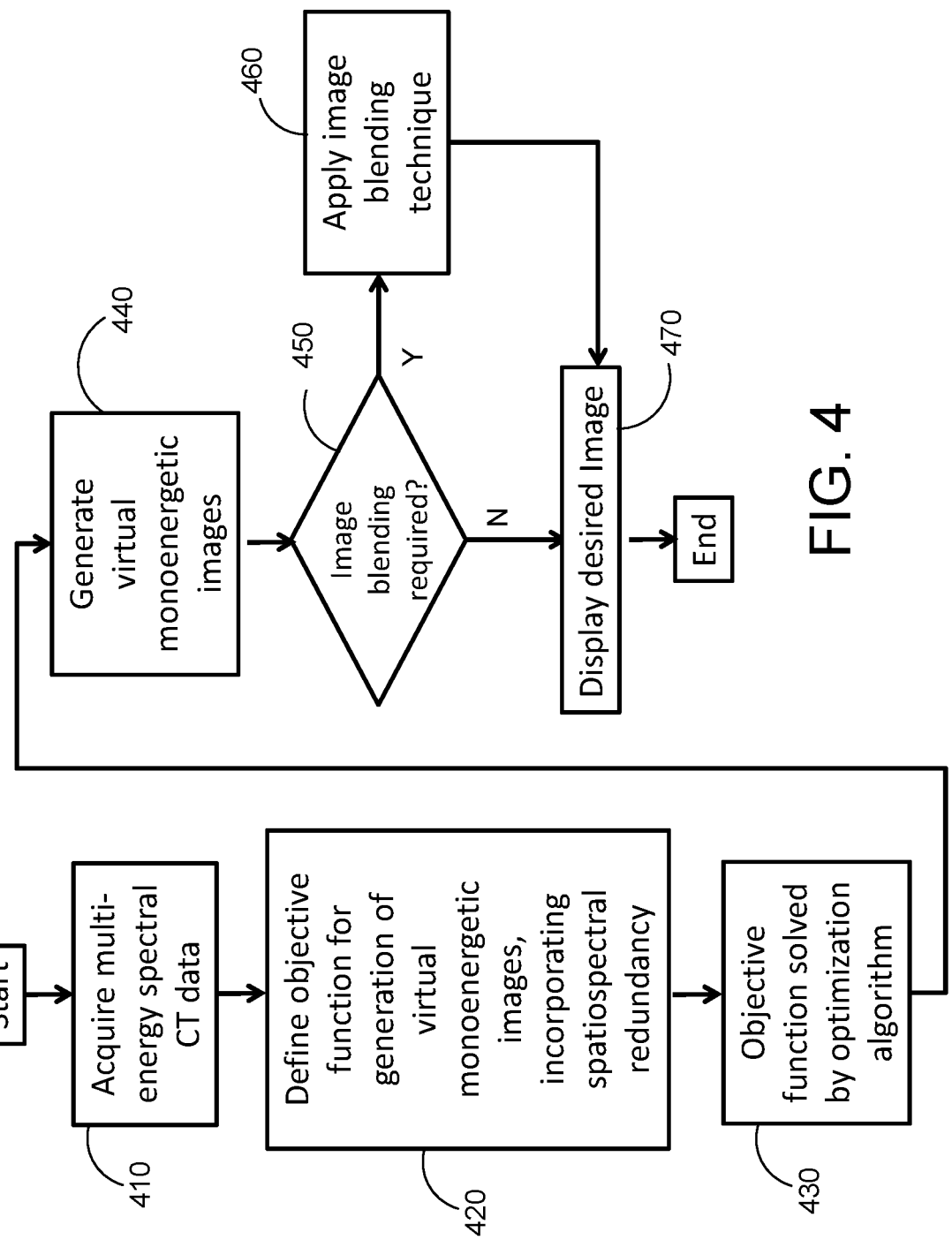
FIG. 4 is a flowchart depicting one example of the framework shown in FIG. 2, where the multi-energy processing refers to generation of virtual monoenergetic images.

Referring now to FIG. 4, a flowchart depicting one example of the framework shown in FIG. 2 is provided. In this case, the multi-energy processing refers to decomposition based on different physical effects or based on basis material, and the like. The output refers to virtual monoenergetic images at a single energy level.

Figure 5:
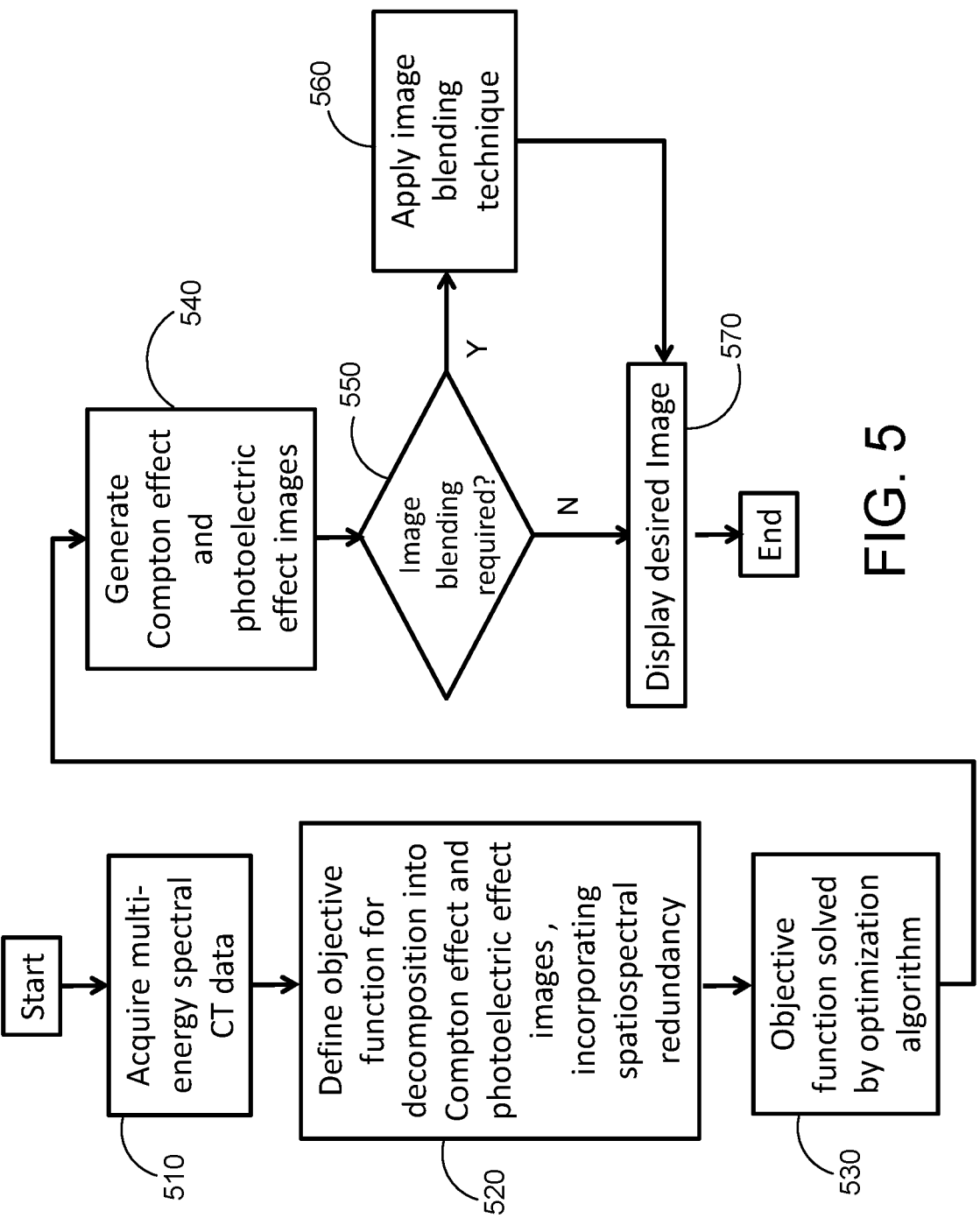
FIG. 5 is a flowchart depicting one example of the framework shown in FIG. 2, where the multi-energy processing refers to physical effects based decomposition.

Referring now to FIG. 5, a flowchart depicting one example of the framework shown in FIG. 2 is provided. In this case, the multi-energy processing refers to decomposition based on different physical effects, and the output refers to images denoting the intensity of different physical effects such as Compton and photoelectric effects.

Figure 6:
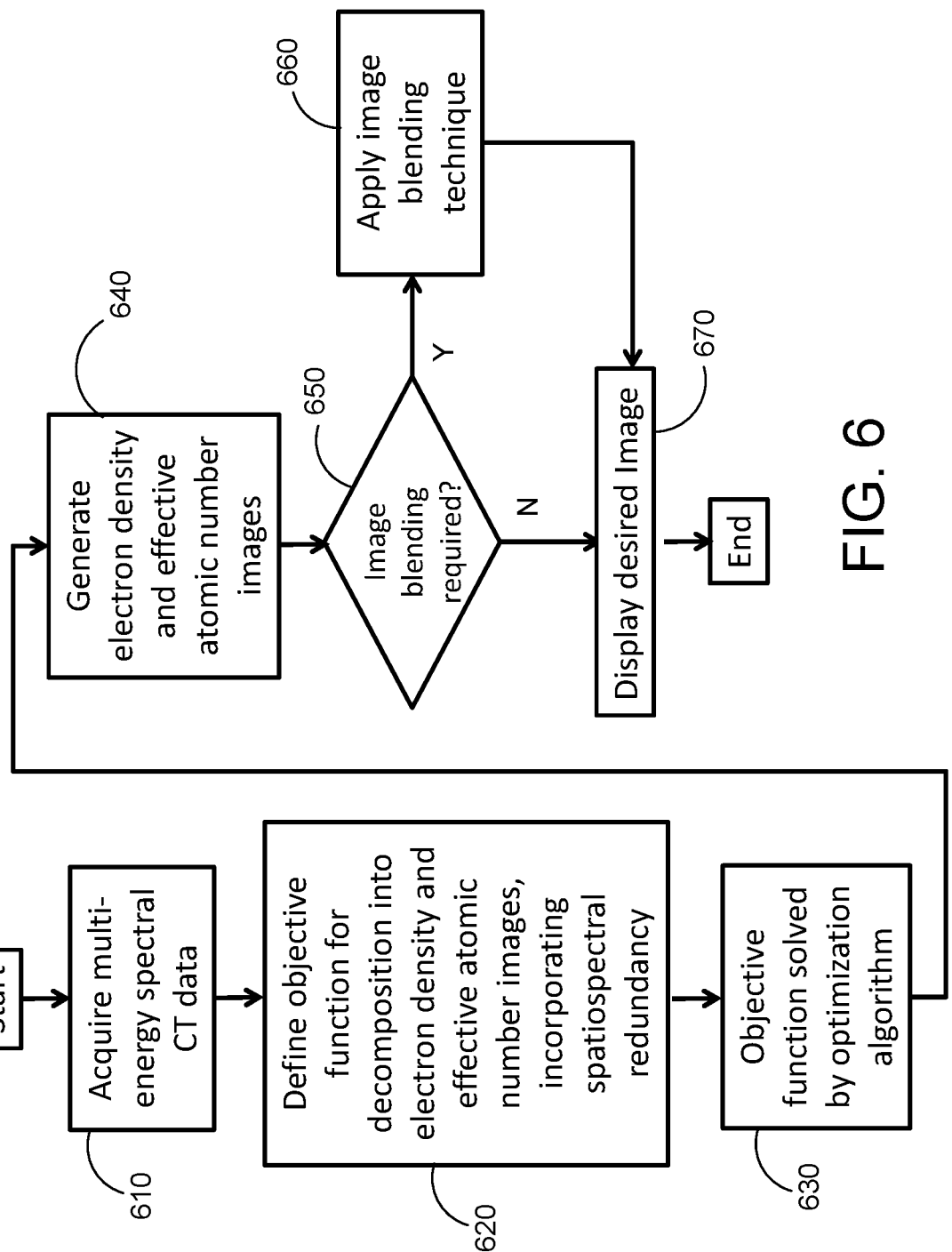
FIG. 6 is a flowchart depicting one example of the framework shown in FIG. 2, where the multi-energy processing refers to electron density and effective atomic number based decomposition.

Referring now to FIG. 6, a flowchart depicting one example of the framework shown in FIG. 2 is provided. In this case, the multi-energy processing refers to decomposition into electron density and effective atomic number images, and the output refers to electron density and effective atomic number images.

Figure 7:
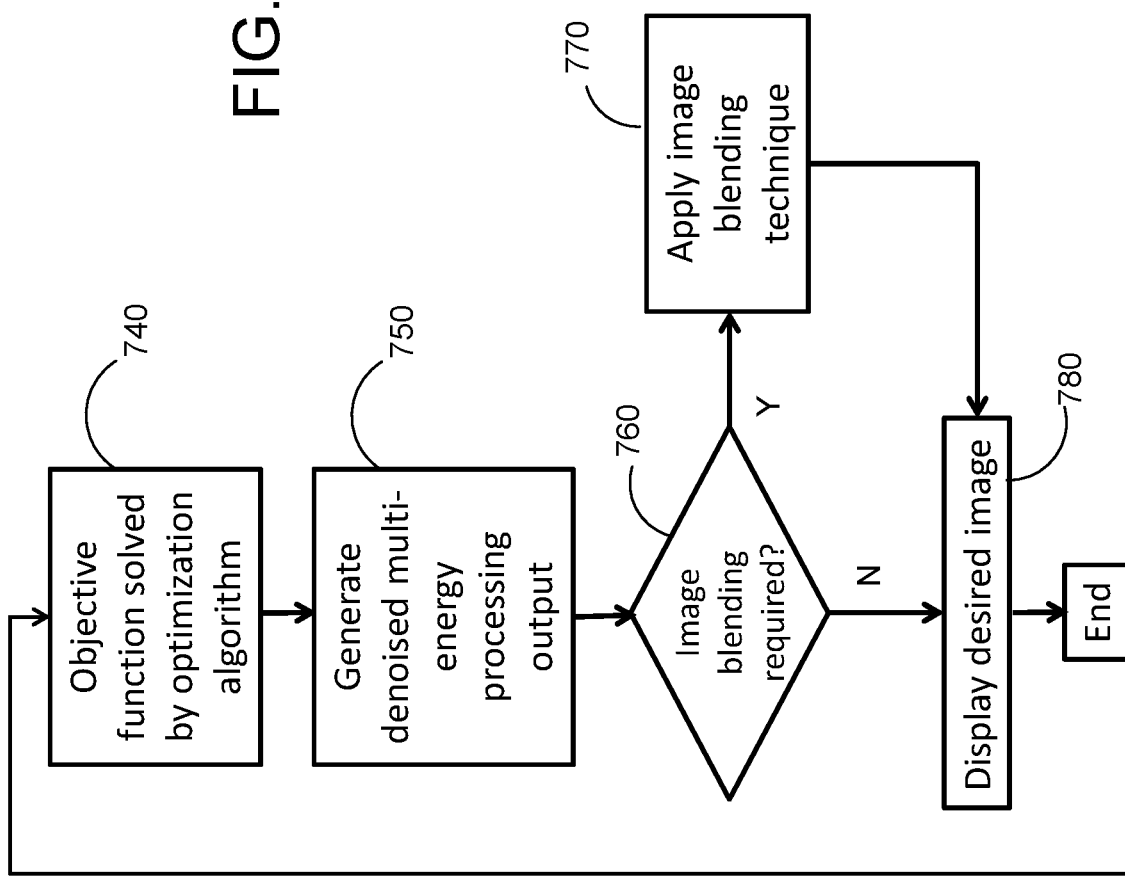
FIG. 7 is a flowchart depicting another configuration of the present disclosure, in which the present disclosure is used to reduce noise and enhance image features (such as CNR) in the output of any multi-energy processing method, such as virtual monoenergetic images, material-specific images, electron density images, or photoelectric effect images.

Referring now to FIG. 7, a flowchart depicting another configuration of the present disclosure is provided. Multi-energy CT image data are acquired at step 710. Standard material decomposition or another relevant multi-energy CT processing algorithm is performed at step 720 to generate output images such as material specific images and virtual monoenergetic images. The denoising of the output from multi-energy processing is then performed at step 730 by designing an objective function which incorporates the spatiospectral redundancy between the decomposition basis images (or images related to decomposition basis images) and the measured multi-energy CT data, and proceeds by the solution to this objective function being performed by an optimization algorithm at 740. The output of multi-energy CT data processing includes, but is not limited to, material specific images, electron density images, photoelectric images and virtual monoenergetic images. The denoised images were then updated based upon the results of the iterative optimization from step 750. The user may select at step 760 to apply a similar blending technique at step 770 using images before and after denoising to maintain the original image texture. A final image or data output reflecting the denoised version of multi-energy CT processing output is displayed at 780.

Applications of multi-energy CT processing include, but are not limited to: kidney stone characterization (determine elemental composition of stones); plaque characterization (determine elemental composition of plaques); bone, plaque, or calcium removal (identify calcified object and virtually remove the calcium signal); virtual non-contrast (identify iodine signal and remove it); differentiation between gout and pseudo-gout (determine elemental composition of crystal within join spaces); virtual mono-energetic images (determine elemental composition of materials in an image and use known attenuation coefficients for those materials to synthesize images at any selected photon energy); rho/Z decomposition, or photoelectric and Compton effects.

In one configuration of the present disclosure, an image formation model is provided. The multi-energy CT images reconstructed from data acquired using different energy spectra are represented using decomposition bases, such as basis material specific images, Compton and photoelectric effect images. As a non-limiting example, for image-based basis material decomposition, the multi-energy CT images are decomposed into a series of material-specific images. Denoting $w_i(n)$ as the value of the i-th decomposition basis image ($1 \leq i \leq M$) for the n-th pixel ($1 \leq n \leq N$), the effective linear attenuation (or CT number) measurements from a spectral CT acquisition can be expressed as follows:

$$\mu_{\textit{eff}}(n, e) = \sum_{i=1}^{M} m(e, i) w_i(n)$$

where $\mu_{\textit{eff}}(n, e)$ denotes the effective linear attenuation coefficients (or CT number) of the e-th energy channel ($1 \leq e \leq E$) and the n-th pixel; $m(e, i)$ is the system matrix element of the i-th decomposition basis ($1 \leq i \leq M$) corresponding to e-th energy spectra setting, and N, M, and E denote the number of pixels, number of basis materials, and number of energy spectra settings for a multi-energy CT acquisition, respectively. w can represent material-specific images, or other decomposition bases such as images denoting intensities of different physical effects, or images of electron density and effective atomic number images.

Images at different energy levels, f, can be represented as a combination of different decomposition basis with:

$$f = \Pi w, f = [f_1^T, f_2^T, \ldots f_E^T]^T, w = [w_1^T, w_2^T, \ldots w_M^T]^T$$

$$\Pi = \Pi_0 \otimes I_{N \times N}, \Pi_0 = \begin{bmatrix} m_{1,1} & m_{1,2} & \cdots & m_{1,M} \\ \vdots & \vdots & \ddots & \vdots \\ m_{E,1} & m_{E,2} & \cdots & m_{E,M} \end{bmatrix}$$

Here, f (vectorized format of $\mu_{\textit{eff}}(n, e)$) represents images of different energy spectra settings. E is the number of energy spectra settings. N is the number of pixels. w (vectorized format of $w_i(n)$ concatenated for different decomposition bases) represents decomposition basis images. M is the number of decomposition bases. Using basis material decomposition as a non-limiting example, w then represents the material specific images (i.e., water/iodine/calcium, etc.) and describes the concentration (mass density or volume fraction in each voxel) of each basis material. Each element $m_{e,m}$ in $\Pi_0$ represents the x-ray attenuation or CT number per volume/mass density for each material at different energy levels, and $\otimes$ is the Kronecker product.

The $\Pi$ represents system matrix can be obtained from either image domain measurements or projection domain measurements using a calibration phantom with material of known material density. It can also assume theoretical values based on physical principles. The matrix representation of $\Pi$ can also include an additional row to account for the volume conservation or mass conservation constraint which allows for solving for M+1 materials. CT images may be reconstructed from x-ray photons within different energy windows/bins acquired using various techniques mentioned previously. These energy windows/bins may be overlapped. Each element/voxel of f represent x-ray attenuation measurements. These measurements may be in the units of CT numbers (unit=Hounsfield unit) or attenuation coefficients (unit=cm^-1).

In one configuration of the present disclosure, for the case of M+1 basis material decomposition using E energy bins, the calibration matrix takes on the form of an E by M matrix. Typically, the number of materials to be decomposed needs to be smaller than the number of available energy settings, i.e., M≤E, as the system matrix $\Pi$ is otherwise rank deficient. By including additional constraints, such as volume conservation or mass conservation, a total of M+1 material-specific images can be calculated. For the case of volume conservation, the (M+1)-th material-specific image can be calculated using $$w_{M+1} = \rho_{M+1} \left(1 - \sum_{i=1}^{M} \frac{w_i}{\rho_i}\right)$$

Where $\rho_i$ represents the mass density of the i-th basis material. The (M+1)-th material (e.g., water) can be later solved by assuming the volume fractions within a voxel of different material add up to unity.

In another configuration of the present disclosure, a similar model to that described above may be used for projection domain data, g.

$$g = A\Pi w, g = [g_1^T, g_2^T, \ldots g_E^T]^T, w = [w_1^T, w_2^T, \ldots w_M^T]^T$$

Where g represents projection data after forward projection operator A. Forward projection operator A is a linear operator when g is already processed with a logarithm operation. A becomes a nonlinear operation for the more general case with g denoting the photon count data or raw energy integrating signal strength.

In one configuration of the present disclosure, material decomposition proceeds by minimizing an objective function:

$$w_0 = \underset{w}{\mathrm{argmin}} \sum_{i=1}^{M} \frac{c\|w_i\|_{TV} + (1-c)\|w_i - \Gamma_i(f_{prior})\|_{TV}}{N_i}, \text{ s.t. } f = \Pi w, w_i = P_i w$$

$$f_{MD}^i(w_i) = c\|W_i\|_{TV} + (1-c)\|w_i - \Gamma_i(f_{prior})\|_{TV}$$

Where $P_i$ denotes a binary diagonal matrix selecting the i-th decomposition basis image $w_i$ from w, $f_{MD}^i$ denotes the regularization term applied to the i-th decomposition basis image $w_i$, c is a parameter that controls the relative weight between total variation (TV) of each decomposition basis image itself, $\|w_i\|_{TV}$, and the difference between the decomposition basis image and its prior image, $\|w_i - \Gamma_i(f_{prior})\|_{TV}$. $\|w_i\|_{TV}$ is a term that directly minimizes the total variation (TV) of each decomposition basis image. The $\|w_i - \Gamma_i(f_{prior})\|_{TV}$ term applies a sparsifying transform to the difference between the decomposition image and its corresponding material prior image. By including $\|w_i - \Gamma_i(f_{prior})\|_{TV}$ as a regularization term, it is assumed that the individual decomposition image ($w_i$) and the basis material prior image $\Gamma_i(f_{prior})$ share structural redundancy, so that after removing the contribution of each decomposition image ($w_i$), the residual image is still sparse after TV transform. $\Gamma_i(f_{prior})$ is a transformation $\Gamma_i$ applied to energy prior image ($f_{prior}$), which may be a low-noise energy prior image, and is a function of material type (ie., for the i-th material). This is represented by:

$$\Gamma_i(f_{prior}) = \frac{f_{prior} - \sum_{j=1, j\neq i}^{M} \mu_{prior,j} w_j}{\mu_{prior,i}}$$

Where $f_{prior}$ is an energy prior image. $\mu_{prior,i}$ represents an empirical calibration coefficient and is a scaling factor that converts the prior spectral CT image to a prior decomposition basis image and can be obtained from the same calibration scan using data from the corresponding energy spectrum. $w_j$ is an optional parameter representing an initial guess for the each material different from the i-th material, which can be set as zero, and gives:

$$\Gamma_i(f_{prior}) = \frac{f_{prior}}{\mu_{prior,i}}$$

When c=1, the algorithm reduces to the TV-penalized material decomposition. For a non-zero value of c (in one nonlimiting example of a non-zero value, c=0.6), the algorithm uses structural similarity between the image and the prior image to perform material decomposition. Standard, direct material decomposition is equivalent to performing decomposition without either regularization terms by only minimizing the data fidelity term from a least-squares sense. $\Gamma_i(f_{prior})$ can also be other types of transformation using $f_{prior}$.

In one example on a photon counting detector (PCD) based CT system, the measured prior spectral CT image $f_{prior}$ may be a high SNR image. On a PCD system such as a research whole-body CT system, the CT image reconstructed using all the available photons of different energy spectra typically has the highest SNR, which can be used as $f_{prior}$. A conventional CT system uses energy integrated detectors (EID). On these systems, an image with higher SNR and reasonable contrast can be used as the prior image. As a nonlimiting example, on a dual energy CT system which uses two tube-detector pairs (Tube A and B), one low-noise CT image (e.g., "tube A" image), or a weighted mixed image between tube A and B sub systems can be used as the prior image. On a dual-source, dual-energy CT system, the tube A and tube B images may be used for material decomposition, with the mixed image between tube A and tube B (mixing ratio=0.5, for example) used as the prior image.

In one configuration of the present disclosure, the data fidelity term can be absorbed into the material decomposition objective function, which gives:

$$\operatorname*{argmin}_{W} \sum_{i=1}^{M} \frac{c\|w_i\|_{TV} + (1-c)\|w_i - f_i(f_{prior})\|_{TV}}{N_i} + \lambda \|f - \Pi w\|_2^2, \text{ s.t. } : w_i = P_i w$$

Where $\lambda \geq 0$ is a parameter that controls the relative preference for the data fidelity term, $\|f - Mw\|_2^2$, versus the regularization term. Data processing may include using different c values ranging from 0 to 1 (with 0.1 increment) depending upon the effect of parameter c on decomposition performance. The denoising performance and decomposition accuracy may be quantified using root-mean-square error (RMSE), which accounts for both noise and bias in the material specific images. The parameter c can be determined by evaluating the bias, noise, and RMSE of the decomposed material specific images based on phantom measurements of known material compositions. The algorithm parameter $\lambda$ controls the preference of data fidelity term over regularization term, and is usually determined empirically. A larger $\lambda$ can be used for high SNR images or high dose scan, while for low SNR scans a smaller $\lambda$ can be used. For example, a user may select a $\lambda$ from $1\times10^2$ to $5\times10^3$ in order to yield desirable denoising performance.

In one configuration of the present disclosure, the objective function can incorporate the synthetization of other multi-energy processing output, such as other decomposition basis images or virtual monoenergetic images. In one configuration of the present disclosure, the optimization problem is solved by an adaptive gradient descent algorithm. In an alternative configuration, the optimization problem is solved by an alternating direction method of multiplier (ADMM) algorithm. Any other appropriate numerical algorithm may be used to solve the optimization problem, such as primal-dual algorithm, conjugate gradient algorithm, Newton's method, or Quasi Newton's method like Broyden-Fletcher-Goldfarb-Shanno algorithm and the like.

In one configuration of the present disclosure, the optimization problem is solved iteratively by an alternating direction method of multiplier (ADMM) algorithm. The ADMM algorithm is a flexible numerical optimization strategy that can be used for a variety of convex optimization problems. It decomposes a compound target optimization problem into a series of relatively easier tasks. With ADMM, the augmented Lagrangian functional for the constrained optimization problem is first constructed as:

$$L(w, w_i, \zeta_i) = \sum_{i=1}^{M} f_{MD}^i(w_i) + \lambda \|f - \Pi w\|_2^2 + \mu \sum_{i=1}^{M} \|w_i - P_i w + \zeta_i\|_2^2$$

where $\zeta_i$ denotes the Lagrangian multiplier vector; $\mu$ is an optimization constant that controls the rate of convergence of the ADMM algorithm and is typically determined empirically. Then, the material specific images, w, are obtained by minimizing the Lagrangian functional. In ADMM, the minimization of $L(w, w_i, \zeta_i)$ is done sequentially with respect to w and $w_i$, followed by an update for $\zeta_i$. In the n-th iteration, the ADMM algorithm resorts to the following:

$$w_n = \operatorname*{argmin}_{w} L(w, w_{i,n-1}, \zeta_{i,n-1})$$

$$w_{i,n} = \operatorname*{argmin}_{w_i} L(w_n, w_i, \zeta_{i,n-1})$$

$$\zeta_{i,n} = \zeta_{i,n-1} + (w_{i,n} - P_i w_n)$$

where $w_n$, $w_{i,n}$ and, $\zeta_{i,n}$ are the current value of w, $w_i$ and $\zeta_n$ in the n-th iteration, respectively.

The update of $w_n$ is a quadratic optimization problem, which has a non-iterative solution as follows:

$$w_n = \left(\frac{\lambda}{\mu}\Pi^T\Pi + \sum_{i=1}^{M} P_i^T P_i\right)^{-1}\left[\frac{\lambda}{\mu}\Pi^T f + \sum_{i=1}^{M} P_i^T(w_{i,n-1} + \zeta_{i,n-1})\right]$$

$$= \left(\frac{\lambda}{\mu}\Pi^T\Pi + I_{M\times N}\right)^{-1}\left[\frac{\lambda}{\mu}\Pi^T f + \sum_{i=1}^{M} P_i^T(w_{i,n-1} + \zeta_{i,n-1})\right]$$

The update of $w_{i,n}$ may include the minimization of a term including $f_{MD}{}^i(w_i)$. In one configuration, this can be performed using an iterative gradient descent routine with backtracking line search. In an alternative configuration, ADMM is used to update $w_{i,n}$. ADMM does not require a sub-problem to be solved exactly to guarantee convergence, and an inexact update will simply slow the overall convergence rate. With an ADMM approach, in the n-th ADMM iteration, it yields:

$$w_{i,n} = w_{i,n-1} - \tau\left[\frac{\partial f_{MD}^i(w_{i,n-1})}{\partial w_{i,n-1}} + 2\mu(w_{i,n-1} - P_i w_n + \zeta_{i,n-1})\right]$$

where the step size $\tau$ can be determined using backtracking line search. Finally, with the new values of $w_n$ and $w_{i,n}$ obtained, $\zeta_{i,n}$ can be updated. The value of $\mu$ affects the relative contribution of the $(\Pi^T\Pi)^{-1}\Pi^T f$ term and that of the $$\sum_{i=1}^{M} P_i^T(w_{i,n-1} + \zeta_{i,n-1})$$

term in the update of $w_n$, which affects the convergence rate for the ADMM iteration. The value of $\mu$ is usually determined empirically. An example is setting $\mu=\lambda$.

In one non-limiting example of the present disclosure, phantom data was acquired on a research, whole-body photon-counting-detector-based CT system and on a dual-source, dual-energy CT system. Phantom results show that the proposed multi-energy processing can reduce the root-mean-square-error of basis material quantification by 75% compared to the standard material decomposition based on matrix inversion, while preserving structural details and image resolution in the material-specific images.

Noise reduction algorithms, especially TV-based algorithms, can change image texture and create patchy looking images. To alleviate this effect, a linear blending technique to combine the output of multi-energy processing from the present method with the standard least-squares based method may be used to maintain the original image texture while reducing noise. The final output $w_{output}$ is then expressed as:

$$w_{output} = \alpha w_1 + (1-\alpha)w_0$$

where $\alpha$ is the blending factor, and may be chosen as any appropriate value, such as 0.9; $w_1$ and $w_0$ denote the output of multi-energy processing obtained by using the present method and standard least-squares based approach, respectively.

In one configuration of the present disclosure, the spectral CT images reconstructed from data acquired using different energy spectra are decomposed into material-specific images. In another configuration of the present disclosure, spectral CT images are decomposed to other decomposition bases. These include, but not limited to, effective atomic number and electron density, photoelectric effect and Compton effect images. In another configuration of the present disclosure, the objective function can incorporate the synthetization of other multi-energy processing output, such as other decomposition basis images or virtual monoenergetic images. A constrained optimization scheme may be used. The synthetization can be performed during or after solving the optimization problem.

In another configuration of the present disclosure, the output images of other multi-energy CT processing methods, such as the decomposition basis images and virtual monoenergetic images, can be processed and denoised using the present disclosure to enhance certain image features, such as reduced noise and enhanced CNR, by minimizing an objective function that exploits the spatiospectral data redundancy between the source multi-energy processing output and the multi-energy CT images.

In one configuration, the following objective function may be used:

$$\hat{x} = \underset{x}{\mathrm{argmin}}[c\|x\|_{TV} + (1-c)\|x - \Gamma(f_{prior})\|_{TV}] + \lambda\|x - x_0\|_2^2 \quad (1)$$

where the operator $\|\cdot\|_{TV}$ calculates the total-variation (TV) of a vector; x represents the multi-energy CT processing output of interest; $x_0$ is the original image output derived from any multi-energy processing methods such as any virtual monoenergetic imaging algorithm. $f_{prior}$ is the low-noise, spectral prior image associated with the same imaging object. $\Gamma(f_{prior})$ is a transformation applied to $f_{prior}$ to convert it to the similar scale and meaning of x. The formulation of $\Gamma(f_{prior})$ can be similar to the one used in previous sections. Using virtual monoenergetic image as a nonlimiting example, x represent the virtual monoenergetic image of interest, $\Gamma(f_{prior})$ can be reduced to $f_{prior}$ itself.

On PCD-CT, the energy threshold-low image can be used as the prior image, since it is generated using all the available photons from a single scan and has the lowest noise level. On the dual-source dual-energy CT, the mixed image between the low and high energy images is generated using all radiation dose applied to the patient. It therefore has lower noise compared to any of the individual tube image and can be used as the spectral prior.

The objective function contains a data fidelity term $\|x-x_0\|_2^2$ and a regularization term $c\|x\|_{TV}+(1-c)\|x-\Gamma(f_{prior})\|_{TV}$, with $\lambda$ controlling the relative contribution of the two terms. The value of is usually determined empirically based on the source image noise level and the desired denoising level. The regularization term can be further separated into two components. The first component $\|x\|_{TV}$ is the conventional TV regularization term. The second component $\|x-\Gamma(f_{prior})\|_{TV}$ promotes spatiospectral sparsity by applying TV transform to the difference image between the virtual monoenergetic image, x, and its corresponding spectral prior image, $\Gamma(f_{prior})$. Therefore, including this term exerts spatiospectral sparsity regularization on x. Finally, c is a parameter ($0 \leq c \leq 1$) that controls the relative preference placed on one term versus the other. The parameter c can be determined based on image resolution evaluation using modulation transfer function and noise texture evaluation using noise power spectra.

The optimization problems shown in Eq. 1 can be solved using a standard iterative solver such as gradient descent algorithm. Denote f(x) as the objective function as, $$f(x)=[c\|x\|_{TV}+(1-c)\|x-\Gamma(f_{prior})\|_{TV}]+\lambda\|x-x_0\|_2^2 \quad (2)$$

and let $x_i$ be the value of x in the i-th iteration. The gradient descent algorithm calculates update x according to the following iteration:

$$x_i = x_{i-1} - \alpha \frac{\partial f(x)}{\partial x}\bigg|_{x_{i-1}} \quad (3)$$

where the step size $\alpha$ can be determined via back tracking line search. The optimization problem can also be solved using other relevant optimization algorithms such as conjugate gradient, ADMM, primal dual algorithm, Newton's method and quasi Newton's method. The objective function can also incorporate the synthetization of other multi-energy CT output such as other decomposition bases or virtual monoenergetic images. Synthetization can also be performed after solving the optimization problem.

In one configuration, a prior knowledge aware iterative denoising technique may utilize structural similarity between a thicker slice and a thinner slice to perform denoising. In a non-limiting example, the spatial redundancy in the slice increment direction is used to reduce image noise while preserving the same resolution, and/or noise texture and/or slice sensitivity profile of the original images. A thin slice image with comparable noise levels as that of a thicker slice image may be produced while taking advantage of reduced partial volume effect of a thin slice image. Low-noise, thin-slice, high-resolution images may be produced to provide better visualization of fine anatomical structures. The method may allow for the diagnostic value of CT images to be improved by satisfying the clinical demands for low image noise and reduced partial volume effect of a thin slice image.

In some configurations, image sharpness, noise texture, and slice profile of the original image is retained before denoising. A non-limiting example of a slice profile includes a cross-section graph of contrast levels across a slice. A thin-slice image may be denoised with a lower noise level, reduced partial volume effect, and the image may retain key pathology visibility. Parameters may be adjusted to achieve a desired level of noise reduction, noise texture, and/or image artifact. Non-limiting example cases where key pathology visibility may be important include non-contrast head CT cases, and the like. Non-limiting example high-resolution CT images that may benefit from reduced noise include thin-slice, high-resolution wrist images, and the like.

Single Energy CT Example(s)

Figure 8:
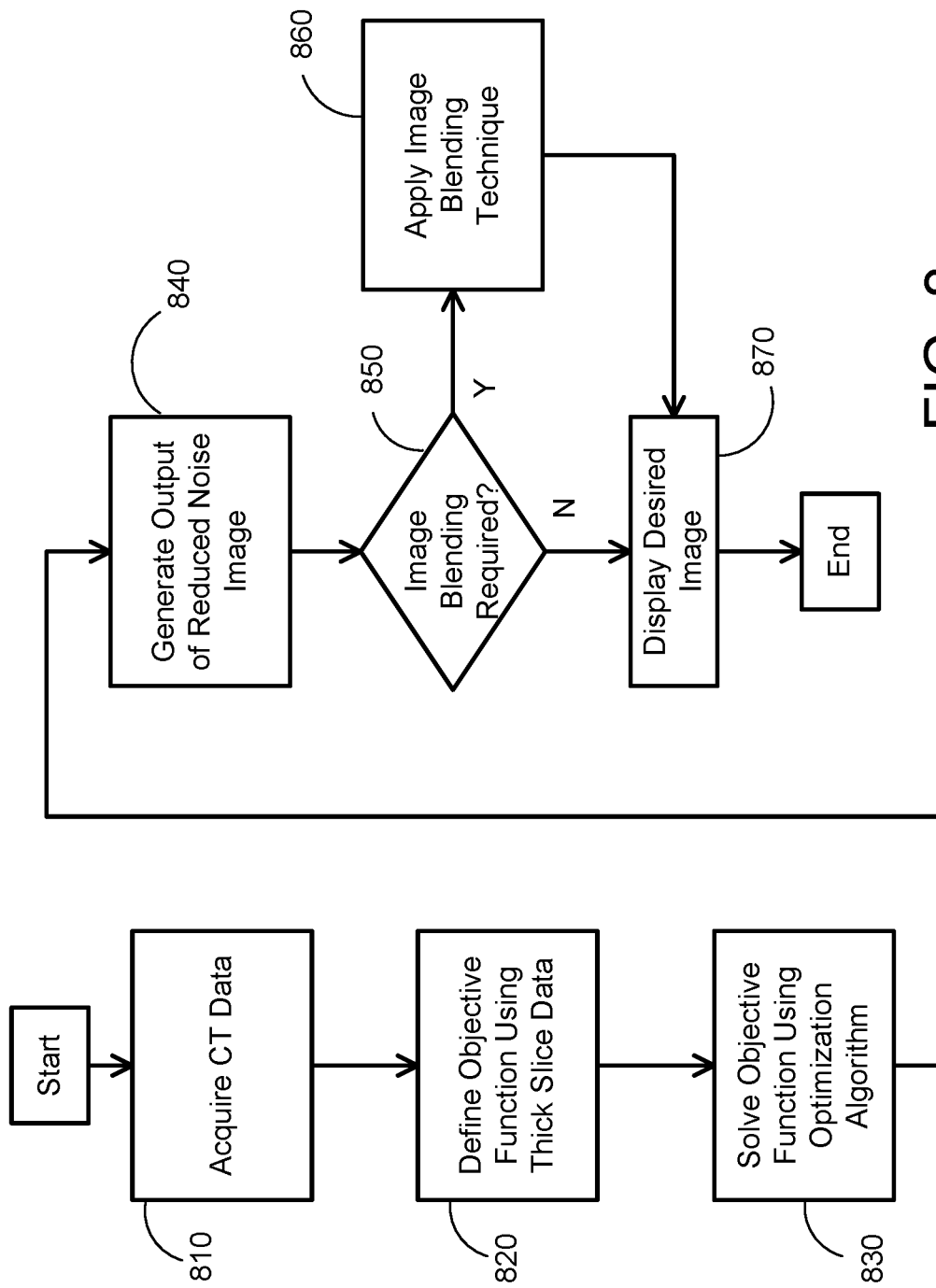
FIG. 8 is a flowchart depicting another configuration of the present disclosure, in which the present disclosure is used to reduce noise and enhance image features (such as CNR) using prior knowledge.

Referring to FIG. 8, a flowchart depicting one configuration of the present disclosure for using prior knowledge is provided. CT image data that includes thick slice data are acquired, or otherwise accessed, at step 810. The denoising of the data is then performed at step 820 by designing an objective function which incorporates the spatial data redundancy between the prior, thick slice, image and the image to be denoised, and proceeds by the solution to this objective function being performed by an optimization algorithm at 830. The denoised images are then updated based upon the results of the iterative optimization at step 840. The user may select at step 850 to apply a similar blending technique at step 860 using images before and after denoising to maintain the original image texture. A final image or data output reflecting the denoised version of input image is displayed at 870. The final image may include higher resolution and lower noise, and may be displayed for a user or stored for future use in an appropriate image storage system.

Equation (1) above may be used where the operator $\|\cdot\|_{TV}$ calculates the total-variation (TV) of a vector; x represents the denoised images; $x_0$ represents the input thin-slice image to be denoised. $f_{prior}$ is the low-noise, prior image at the same spatial location, or a nearby spatial location, but with a larger slice thickness. A nearby spatial location may be defined by a user as being within a certain selected distance, or a certain number of slices. The objective function contains a data fidelity term $\|x-x_0\|_2^2$ and a regularization term $c\|x\|_{TV}+(1-c)\|x-f_{prior}\|_{TV}$, with $\lambda$ controlling the relative contribution of the two terms. The regularization term can be further separated into two components. The first component $\|x\|_{TV}$ penalizes the total variation of the image, while the second component $\|x-f_{prior}\|_{TV}$ exploits the structural similarity between the prior image and the image to be denoised by promoting the sparsity in their difference image. The method may be implemented in the time domain.

The method for denoising using a larger slice thickness may be applied to images acquired on various CT systems from different vendors and can be utilized for all types of CT applications including for any body part or pathology. Iterative reconstruction techniques may also be employed with the method such as those provided by system vendors or other research techniques to further lower image noise.

Example Clinical Application

In one configuration, the system and method may be used to grade cartilage health. Conventional techniques are invasive and require multiple instruments. The system and method of the present disclosure may provide for quantitative Glycosaminoglycans (GAG) information, such as by using a targeted contrast agent at a high spatial resolution. This may also allow for assessing osteoarthritis (OA). PCD-CT acquires spectral data, which may be used to quantify the mass density of specific K-edge contrast agents, such as gadolinium, which in turn may be used to mark the GAG levels within a voxel of interest. Dotarem (Gd-based anionic contrast, FDA approved for MRI intravenous administration) density may be quantified using a material decomposition process, as described above.

CT Systems

Figure 9A:
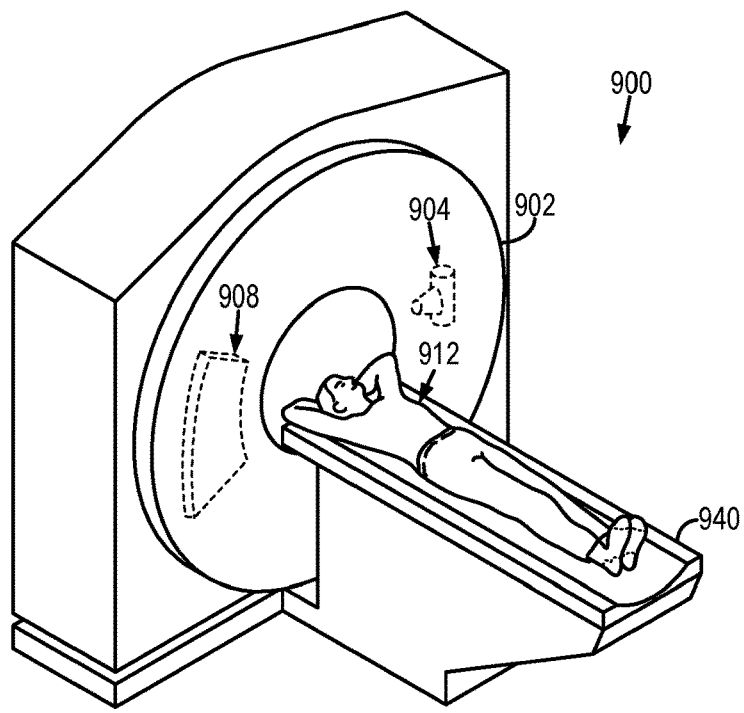
FIGS. 9A and 9B illustrate an example CT system, which may be a single-energy or a multi-energy CT system.
Figure 9B:
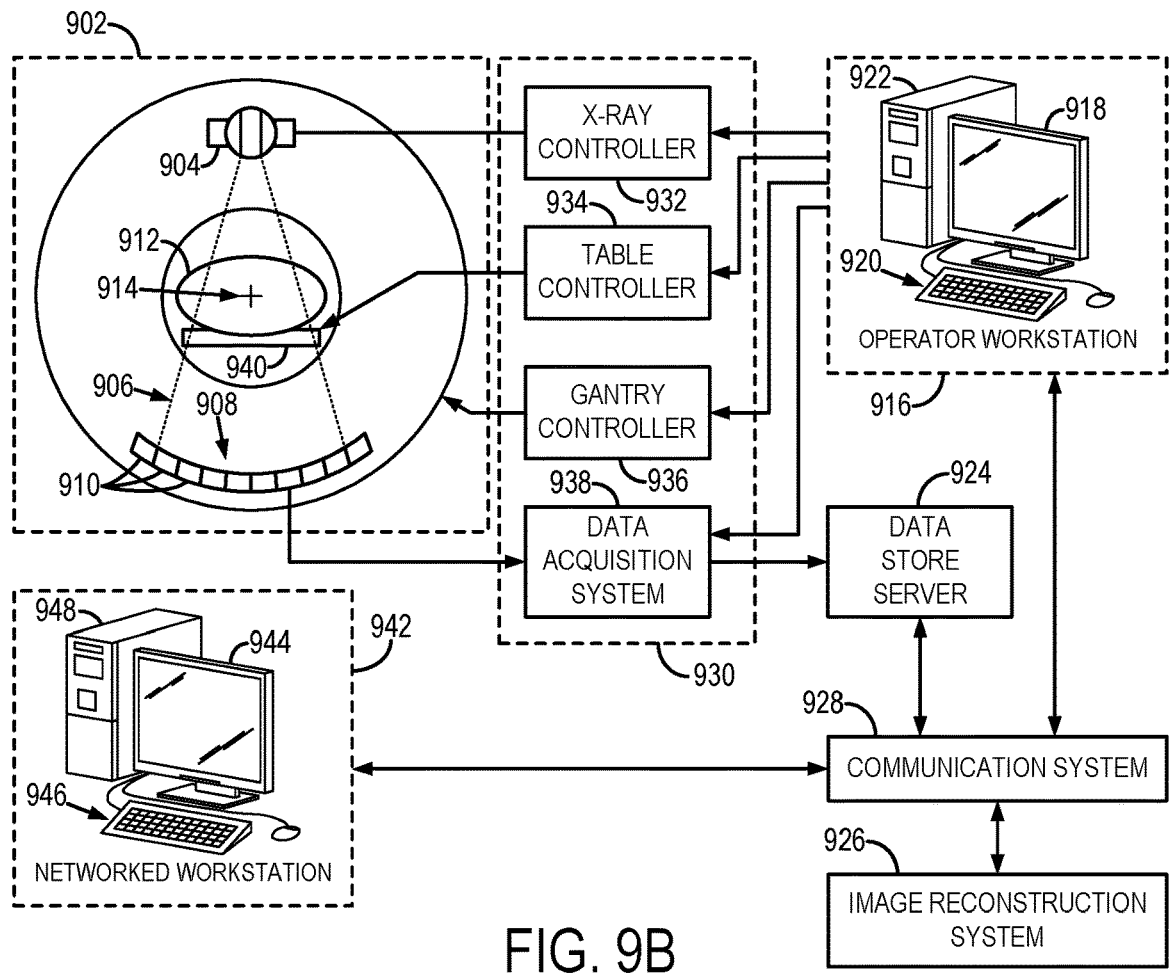

Referring particularly now to FIGS. 9A and 9B, an example of an x-ray computed tomography ("CT") imaging system 900 is illustrated. The CT system includes a gantry 902, to which at least one x-ray source 904 is coupled. The x-ray source 904 projects an x-ray beam 906, which may be a fan-beam or cone-beam of x-rays, towards a detector array 908 on the opposite side of the gantry 902. The detector array 908 includes a number of x-ray detector elements 910. Together, the x-ray detector elements 910 sense the projected x-rays 906 that pass through a subject 912, such as a medical patient or an object undergoing examination, that is positioned in the CT system 900. Each x-ray detector element 910 produces an electrical signal that may represent the intensity of an impinging x-ray beam and, hence, the attenuation of the beam as it passes through the subject 912. In some configurations, each x-ray detector 910 is capable of counting the number of x-ray photons that impinge upon the detector 910. In some configurations the system can include a second x-ray source and a second x-ray detector (not shown) operable at a different energy level than x-ray source 904 and detector 910. Any number of x-ray sources and corresponding x-ray detectors operable at different energies may be used, or a single x-ray source 904 may be operable to emit different energies that impinge upon detector 910. During a scan to acquire x-ray projection data, the gantry 902 and the components mounted thereon rotate about a center of rotation 914 located within the CT system 900.

The CT system 900 also includes an operator workstation 916, which typically includes a display 918; one or more input devices 920, such as a keyboard and mouse; and a computer processor 922. The computer processor 922 may include a commercially available programmable machine running a commercially available operating system. The operator workstation 916 provides the operator interface that enables scanning control parameters to be entered into the CT system 900. In general, the operator workstation 916 is in communication with a data store server 924 and an image reconstruction system 926. By way of example, the operator workstation 916, data store sever 924, and image reconstruction system 926 may be connected via a communication system 928, which may include any suitable network connection, whether wired, wireless, or a combination of both. As an example, the communication system 928 may include both proprietary or dedicated networks, as well as open networks, such as the internet.

The operator workstation 916 is also in communication with a control system 930 that controls operation of the CT system 900. The control system 930 generally includes an x-ray controller 932, a table controller 934, a gantry controller 936, and a data acquisition system 938. The x-ray controller 932 provides power and timing signals to the x-ray source 904 and the gantry controller 936 controls the rotational speed and position of the gantry 902. The table controller 934 controls a table 940 to position the subject 912 in the gantry 902 of the CT system 900.

The DAS 938 samples data from the detector elements 910 and converts the data to digital signals for subsequent processing. For instance, digitized x-ray data are communicated from the DAS 938 to the data store server 924. The image reconstruction system 926 then retrieves the x-ray data from the data store server 924 and reconstructs an image therefrom. The image reconstruction system 926 may include a commercially available computer processor, or may be a highly parallel computer architecture, such as a system that includes multiple-core processors and massively parallel, high-density computing devices. Optionally, image reconstruction can also be performed on the processor 922 in the operator workstation 916. Reconstructed images can then be communicated back to the data store server 924 for storage or to the operator workstation 916 to be displayed to the operator or clinician.

The CT system 900 may also include one or more networked workstations 942. By way of example, a networked workstation 942 may include a display 944; one or more input devices 946, such as a keyboard and mouse; and a processor 948. The networked workstation 942 may be located within the same facility as the operator workstation 916, or in a different facility, such as a different healthcare institution or clinic.

The networked workstation 942, whether within the same facility or in a different facility as the operator workstation 916, may gain remote access to the data store server 924 and/or the image reconstruction system 926 via the communication system 928. Accordingly, multiple networked workstations 942 may have access to the data store server 924 and/or image reconstruction system 926. In this manner, x-ray data, reconstructed images, or other data may be exchanged between the data store server 924, the image reconstruction system 926, and the networked workstations 942, such that the data or images may be remotely processed by a networked workstation 942. This data may be exchanged in any suitable format, such as in accordance with the transmission control protocol ("TCP"), the internet protocol ("IP"), or other known or suitable protocols.

Computer System

Figure 10:
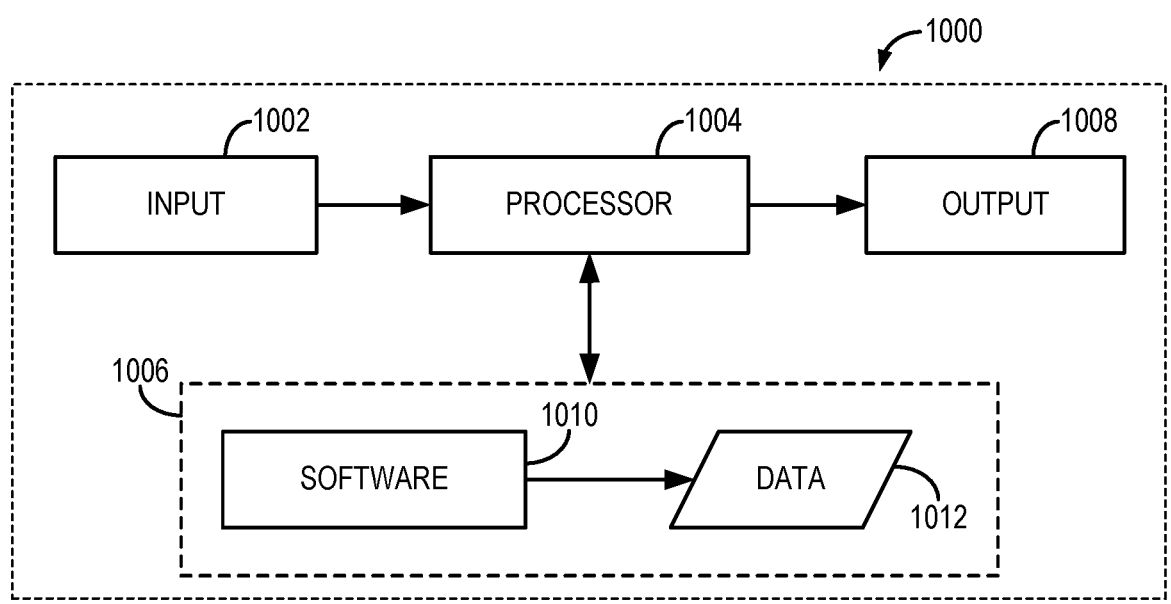
FIG. 10 is a block diagram of an example computer system, which can implement embodiments described in the present disclosure.

Referring now to FIG. 10, a block diagram of an example of a computer system 1000 that can perform the methods described in the present disclosure is shown. The computer system 1000 generally includes an input 1002, at least one hardware processor 1004, a memory 1006, and an output 1008. Thus, the computer system 1000 is generally implemented with a hardware processor 1004 and a memory 1006.

In some embodiments, the computer system 1000 can be a workstation, a notebook computer, a tablet device, a mobile device, a multimedia device, a network server, a mainframe, one or more controllers, one or more microcontrollers, or any other general-purpose or application-specific computing device.

The computer system 1000 may operate autonomously or semi-autonomously, or may read executable software instructions from the memory 1006 or a computer-readable medium (e.g., a hard drive, a CD-ROM, flash memory), or may receive instructions via the input 1002 from a user, or any another source logically connected to a computer or device, such as another networked computer or server. Thus, in some embodiments, the computer system 1000 can also include any suitable device for reading computer-readable storage media.

In general, the computer system 1000 is programmed or otherwise configured to implement the methods and algorithms described in the present disclosure. For instance, the computer system 1000 can be programmed to denoised images or otherwise improve the image quality of images acquired with a CT system in accordance with embodiments described in the present disclosure.

The input 1002 may take any suitable shape or form, as desired, for operation of the computer system 1000, including the ability for selecting, entering, or otherwise specifying parameters consistent with performing tasks, processing data, or operating the computer system 1000. In some aspects, the input 1002 may be configured to receive data, such as data acquired with a CT system. Such data may be processed as described above to improve the image quality of an input image based by exploiting redundant data in an iterative optimization algorithm, such as those described above. In addition, the input 1002 may also be configured to receive any other data or information considered useful for generating images with improved image quality, such as reduced noise, using the methods described above.

Among the processing tasks for operating the computer system 1000, the one or more hardware processors 1004 may also be configured to carry out any number of post-processing steps on data received by way of the input 1002.

The memory 1006 may contain software 1010 and data 1012, such as data acquired with a CT system, and may be configured for storage and retrieval of processed information, instructions, and data to be processed by the one or more hardware processors 1004. In some aspects, the software 1010 may contain instructions directed to generating a denoised image, or an image with otherwise improved image quality, by exploiting redundant data between two input images having spatial redundancy, spectral redundancy, or spatiospectral redundancy.

In addition, the output 1008 may take any shape or form, as desired, and may be configured for displaying images, such as denoised image, in addition to other desired information.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for reducing noise in an image obtained using a computed tomography (CT) system, the method comprising:
   (a) accessing with a computer system, CT data acquired from a subject using the CT system, wherein the CT data comprise a first image of the subject of a first image type and a second image of the subject of a second image type that is different from the first image type, wherein the first image and the second image contain redundant data;
   (b) generating with the computer system a denoised image having reduced noise relative to the first image by:
      inputting the first image and the second image to an objective function that includes a regularization term that exploits the redundant data in the first image and the second image; and
      minimizing the objective function in order to iteratively denoise the first image, generating output as the denoised image.

2. The method of claim 1, wherein the regularization term includes a first component and a second component, wherein the first component of the regularization term comprises a total variation of the first image and the second component of the regularization term exploits the redundant data in the first image and the second image by promoting sparsity in a difference between the first image and the second image.

3. The method of claim 1, wherein the first image has a thinner slice thickness than the second image, and the redundant data comprise structural similarities between the first image and the second image.

4. The method of claim 3, wherein the structural similarities include spatial redundancy in a slice increment direction.

5. The method of claim 1, wherein the denoised image has at least one of an image resolution, a noise texture, or a slice sensitivity profile that matches with the first image.

6. The method of claim 1, wherein the second image is located at a same spatial location as the first image.

7. The method of claim 1, wherein the CT data comprise multi-energy spectral CT data, the second image is a multi-energy image, and the redundant data comprises one of spectral redundancy and spatiospectral redundancy between the first image and the second image.

8. The method of claim 7, wherein the first image comprises one of a material-specific image, a virtual monoenergetic image, an electron density image, an effective atomic number image, a Compton effect image, or a photoelectric effect image.

9. The method of claim 1, wherein the objective function is minimized iteratively using at least one of an alternating direction method of multiplier (ADMM) algorithm, a gradient descent algorithm, a primal-dual algorithm, a conjugate gradient algorithm, Newton's method, and Quasi Newton's method like Broyden-Fletcher-Goldfarb-Shanno algorithm.

10. The method of claim 1, wherein generating the denoised image with the computer system further comprises blending the denoised image with another image of the subject produced from the CT data in order to achieve a natural image appearance and noise texture in the denoised image.

11. The method of claim 10, wherein the denoised image and the another image are blended based on a blending parameter that indicates a strength of the blending.

12. The method of claim 10, wherein the denoised image and the another image are blended using a linear blending.

13. The method of claim 1, wherein:
   the CT data comprise multi-energy CT data;
   the objective function is configured to include M materials, such that the first image is input for each of the M materials; and
   at least one of physical constraints, chemical constraints, volume conservation or mass conservation are included in the objective function to provide for performing material decomposition on M+1 materials.

14. A method for reducing noise in an image obtained using a computed tomography (CT) system, the method comprising:
   (a) accessing with a computer system, CT data acquired from a subject using the CT system, wherein the CT data comprise a first image of the subject and a second image of the subject, wherein the first image and the second image contain redundant data, wherein first image has a thinner slice thickness than the second image, and the redundant data comprise structural similarities between the first image and the second image;
   (b) generating with the computer system a denoised image having reduced noise relative to the first image by:
      inputting the first image and the second image to an objective function that includes a regularization term that exploits the redundant data in the first image and the second image; and
      minimizing the objective function in order to iteratively denoise the first image, generating output as the denoised image.

15. The method of claim 14, wherein the structural similarities include spatial redundancy in a slice increment direction.

16. A method for reducing noise in an image obtained using a computed tomography (CT) system, the method comprising:
   (a) accessing with a computer system, CT data acquired from a subject using the CT system, wherein the CT data comprise a first image of the subject and a second image of the subject, wherein the first image and the second image contain redundant data;

(b) generating with the computer system a denoised image having reduced noise relative to the first image by:

inputting the first image and the second image to an objective function that includes a regularization term that exploits the redundant data in the first image and the second image;

minimizing the objective function in order to iteratively denoise the first image, generating output as the denoised image; and wherein generating the denoised image with the computer system further comprises blending the denoised image with another image of the subject produced from the CT data in order to achieve a natural image appearance and noise texture in the denoised image.

17. The method of claim 16, wherein the denoised image and the another image are blended based on a blending parameter that indicates a strength of the blending.

18. The method of claim 16, wherein the denoised image and the another image are blended using a linear blending.

* * * * *

UNITED STATES PATENT AND TRADEMARK OFFICE
CERTIFICATE OF CORRECTION

| | |
|---|---|
| PATENT NO. | : 12,056,796 B2 |
| APPLICATION NO. | : 17/256404 |
| DATED | : August 6, 2024 |
| INVENTOR(S) | : Shengzhen Tao et al. |

It is certified that error appears in the above-identified patent and that said Letters Patent is hereby corrected as shown below:

In the Specification

Column 14, Line 52, "of is" should be --of $\lambda$ is--.

Signed and Sealed this
Nineteenth Day of November, 2024

Katherine Kelly Vidal
*Director of the United States Patent and Trademark Office*